United States Patent
Ben Ari (10) Patent No.: US 10,495,608 B2
(45) Date of Patent: Dec. 3, 2019

(54) SYSTEM AND METHOD FOR DETECTING WEAKENING OF THE ADHESION STRENGTH BETWEEN STRUCTURAL ELEMENTS

(71) Applicant: Elbit Systems Ltd., Haifa (IL)

(72) Inventor: Meir Ben Ari, Haifa (IL)

(73) Assignee: ELBIT SYSTEMS LTD., Haifa (IL)

( * ) Notice: Subject to any disclaimer, the term of this patent is extended or adjusted under 35 U.S.C. 154(b) by 0 days.

(21) Appl. No.: 16/326,955

(22) PCT Filed: Aug. 20, 2017

(86) PCT No.: PCT/IL2017/050923
§ 371 (c)(1),
(2) Date: Feb. 21, 2019

(87) PCT Pub. No.: WO2018/037399
PCT Pub. Date: Mar. 1, 2018

(65) Prior Publication Data
US 2019/0212301 A1    Jul. 11, 2019

(30) Foreign Application Priority Data

Aug. 21, 2016 (IL) .......................................... 247408

(51) Int. Cl.
*G01N 19/04* (2006.01)
*G01N 29/04* (2006.01)
(Continued)

(52) U.S. Cl.
CPC ........... *G01N 29/043* (2013.01); *G01N 19/04* (2013.01); *G01N 29/00* (2013.01);
(Continued)

(58) Field of Classification Search
CPC .. G01N 19/04; B29C 65/8215; G01M 5/0033
(Continued)

(56) References Cited

U.S. PATENT DOCUMENTS 3,564,903 A    2/1971  Woodmansee et al.
3,850,033 A    11/1974 Schmitt
(Continued)

FOREIGN PATENT DOCUMENTS

CN    102207449    10/2011
CN    104019968    9/2014
(Continued)

OTHER PUBLICATIONS

International Search Report of PCT Application No. PCT/IL2017/050923, dated Nov. 28, 2017.

*Primary Examiner* — Herbert K Roberts
(74) *Attorney, Agent, or Firm* — Pearl Cohen Zedek Latzer Baratz LLP (57) ABSTRACT

Aspects of the invention are directed to a method and a system for detecting weakening of the adhesion strength between two or more joint surfaces of two or more structural elements. The system includes one or more Load Pins (LPs) and a controller. The one or more LPs may be inserted through the two or more structural elements such, perpendicular to the two or joint surfaces, such that no shear load is initially sensed by the LP. The system further includes a controller be configured to: upon receiving from the one or more LPs a shear load value, detect the weakening of the adhesion strength between the two or more joint surfaces.

12 Claims, 5 Drawing Sheets

(51) Int. Cl.
  *G01N 29/00* (2006.01)
  *B29C 65/82* (2006.01)
  *G01M 5/00* (2006.01)

(52) U.S. Cl.
  CPC ....... *B29C 65/8215* (2013.01); *G01M 5/0033* (2013.01); *G01N 2291/0258* (2013.01); *G01N 2291/02827* (2013.01)

(58) Field of Classification Search
  USPC ...................................................... 73/150 A
  See application file for complete search history.

(56) References Cited

U.S. PATENT DOCUMENTS

| | | | |
|---|---|---|---|
| 4,010,641 A * | 3/1977 | Krieger, Jr. | G01B 7/24 73/150 A |
| 4,161,114 A | 7/1979 | Kraeutle | |
| 4,184,373 A | 1/1980 | Evans et al. | |
| 4,479,386 A | 10/1984 | Beggs et al. | |
| 4,538,462 A | 9/1985 | Hartog et al. | |
| 4,548,083 A | 10/1985 | Schuerer et al. | |
| 4,854,494 A | 8/1989 | Von Raben | |
| 4,862,740 A | 9/1989 | Lanier | |
| 4,893,513 A | 1/1990 | Schroeder et al. | |
| 5,111,701 A | 5/1992 | Klein | |
| 5,144,845 A | 9/1992 | Pyke | |
| 5,176,028 A | 1/1993 | Humphrey | |
| 5,184,516 A | 2/1993 | Blazic et al. | |
| 5,201,230 A | 4/1993 | Sakakibara | |
| 5,245,293 A | 9/1993 | Runner | |
| 5,265,475 A | 11/1993 | Messinger et al. | |
| 5,559,329 A | 9/1996 | Joseph et al. | |
| 5,747,698 A | 5/1998 | Spillman, Jr. et al. | |
| 5,814,729 A | 9/1998 | Wu et al. | |
| 5,841,034 A | 11/1998 | Ball | |
| 6,216,531 B1 * | 4/2001 | Zhou | G01N 3/04 73/150 A |
| 6,220,102 B1 | 4/2001 | Liao | |
| 6,354,152 B1 * | 3/2002 | Herlik | G01N 29/223 73/597 |
| 6,513,374 B2 | 2/2003 | Goh et al. | |
| 6,799,126 B1 | 9/2004 | Ratcliffe et al. | |
| 7,017,421 B2 | 3/2006 | Kehlenbach | |
| 7,041,960 B2 | 5/2006 | Sato | |
| 7,277,162 B2 | 10/2007 | Williams et al. | |
| 7,283,693 B2 | 10/2007 | Menendez Martin et al. | |
| 7,549,337 B2 | 6/2009 | Sato et al. | |
| 7,623,974 B2 | 11/2009 | Cipra | |
| 7,644,636 B2 | 1/2010 | Gregory et al. | |
| 7,669,467 B2 | 3/2010 | Breuer et al. | |
| 7,687,764 B1 | 3/2010 | Knapp | |
| 7,735,711 B2 | 6/2010 | Farassat | |
| 7,739,918 B1 | 6/2010 | Lapeyronnie et al. | |
| 7,917,311 B2 | 3/2011 | Finkel et al. | |
| 8,024,980 B2 | 9/2011 | Arms et al. | |
| 8,202,378 B2 | 6/2012 | Barrett et al. | |
| 8,343,298 B2 | 1/2013 | Rawlings et al. | |
| 8,413,485 B2 | 4/2013 | Bach et al. | |
| 8,641,845 B2 | 2/2014 | Bruck | |
| 8,766,511 B2 | 7/2014 | Duce et al. | |
| 9,261,419 B2 | 2/2016 | Kempainen et al. | |
| 9,261,444 B1 | 2/2016 | Sutherland et al. | |
| 2003/0219059 A1 | 11/2003 | Scott | |
| 2005/0183517 A1 | 8/2005 | Whitty et al. | |
| 2008/0127752 A1 | 6/2008 | Nakano et al. | |
| 2015/0185128 A1 | 7/2015 | Chang et al. | |
| 2016/0076984 A1 * | 3/2016 | Nick | G01N 3/24 73/842 |

FOREIGN PATENT DOCUMENTS

| | | |
|---|---|---|
| CN | 104181000 | 12/2014 |
| DE | 102009027807 | 3/2011 |
| DE | 102009043698 | 4/2011 |
| DE | 102011084579 | 4/2013 |
| EP | 2568280 | 3/2013 |
| GB | 2145515 | 3/1985 |
| JP | S60222749 | 11/1985 |
| JP | S61120946 | 6/1986 |
| JP | H0886732 | 4/1996 |
| JP | 2004212210 | 7/2004 |
| WO | WO 0046593 | 8/2000 |
| WO | WO 0139253 | 5/2001 |
| WO | WO 0175418 | 10/2001 |
| WO | WO 0241195 | 5/2002 |
| WO | WO 05031501 | 4/2005 |
| WO | WO 05043107 | 5/2005 |
| WO | WO 05081930 | 9/2005 |
| WO | WO 06111360 | 10/2006 |
| WO | WO 07018845 | 2/2007 |
| WO | WO 08068761 | 6/2008 |
| WO | WO 08098376 | 8/2008 |
| WO | WO 08127781 | 10/2008 |
| WO | WO 09049733 | 4/2009 |
| WO | WO 10005647 | 1/2010 |
| WO | WO 10009340 | 1/2010 |
| WO | WO 10064216 | 6/2010 |
| WO | WO 11016857 | 2/2011 |
| WO | WO 11131922 | 10/2011 |
| WO | WO 11160102 | 12/2011 |
| WO | WO 12050803 | 4/2012 |
| WO | WO 12141779 | 10/2012 |
| WO | WO 14080677 | 5/2014 |
| WO | WO 15009309 | 1/2015 |
| WO | WO 15091390 | 6/2015 |
| WO | WO 15158952 | 10/2015 |

* cited by examiner

SYSTEM AND METHOD FOR DETECTING WEAKENING OF THE ADHESION STRENGTH BETWEEN STRUCTURAL ELEMENTS

CROSS-REFERENCE TO RELATED APPLICATIONS

This application is a National Phase Application of PCT International Application No. PCT/IL2017/050923, International Filing Date Aug. 20, 2017, entitled "SYSTEM AND METHOD FOR DETECTING WEAKENING OF THE ADHESION STRENGTH BETWEEN STRUCTURAL ELEMENTS", published on Mar. 1, 2018, under publication No. WO 2018/037399, which claims priority of Israel Patent Application No. 247408, filed on Aug. 21, 2016, all of which are hereby incorporated by reference in their entireties.

BACKGROUND OF THE INVENTION

Adhering structural elements using various glues is a widely used method of attachment, in particular of structural elements made from two different types of materials, for example, a composite material and a metal. One of the major problems of such an attachment is the separation or partial separation of the two structural elements due to weakening of the adhesion strength between joint surfaces of the structural elements. This separation or weakening is difficult to detect, in particular during the service life of the structural elements. For example, when the two structural elements are included in a vehicle (e.g., an aircraft, maritime vessel or a car) it is almost impossible to detect the weakening when the vehicle is on the move (e.g., drive, dive, sail or fly).

Currently known methods use load pins (LPs) for measuring loads (e.g., dynamic loads) in structures. The LPs are mounted to the structure such that the LPs are carrying loads derive from the loads acting on the joint structure. Accordingly, such an LP measures, in high accuracy, dynamic loads acting on the structure. For example, an LP located in a wing of an aircraft will measure dynamic loads acting on the wing during flight.

When coming to detect separation or weakening of the adhesion strength between two elements (e.g., two elements in a wing) a different approach may be taken. Measuring the actual loads acting on the entire joint structure (e.g., wing) cannot indicate if a separation or weakening of the adhesion has occur since it does not measure the adhesion itself. While the joint structure may be heavily loaded the adhesion may still hold the two elements without a failure.

There are several known methods of detecting separation or weakening using direct measurements of the adhesion strength by placing sensors inside an adhesion layer between the two structural elements. A strain gauge (e.g., piezoelectric device) may be embedded in the adhesion layer, directly sensing changes in loads acting in the adhesion layer. This method is limited to the area of which the sensor is inserted and may weaken the adhesion strength by inserting an alien body into the adhesion layer. Additional method is the use of acoustic sensors placed at various areas in the structural elements. Due to the size of the acoustic sensors and the accompanied equipment, this method is very limited and cannot be applied in structures having limited spacing and accessibility that are unapproachable and located in closed assemblies. Additionally, acoustic methods can be used only when the assembly (the vehicle) is stationary.

Accordingly, there is a need for a simple system for measuring separation or weakening of the adhesion between two or more elements in a joint structure. Such a system according to some embodiments of the present invention may use LPs to indirectly detect a separation or weakening of the adhesion between two or more elements in a joint structure. An LP according to some embodiments of the present invention may be inserted to the joint structure such that the LPs itself does not measure the dynamic loads acting on the joint structure and initially (when the adhesion strength is suffice for holding the joint structure) no load at all is acting on the LP even if the joint structure is dynamically loaded.

SUMMARY OF THE INVENTION

There is a need for a reliable system and a method for detecting separation or weakening in adhesion strength between joint surfaces of structural elements, during the service life of a structure. There is further a need for a system for detecting unexpected rapid separation of two or more adhered structural elements, caused by unexpected loads (e.g., external loads) acting on the two or more adhered structural elements. In particular there is a need for a system that may alert the initiation of separation process (e.g., partial separation or weakening) before the structure fails. This is particularly critical in vehicles when the vehicle is on the move, for example, when an Unmanned Aerial Vehicle (UAV) is flying or a race car is racing or a submarine is diving. A system according to embodiments of the invention may use one or more Load Pins (LPs) for sensing in real time weakening in the adhesion strength between two structural elements, thus alerting that a critical damage may occur prior to a complete failure of the adhesion. An LP according to embodiments of the invention is sensing transducer that may include a sensor inserted inside a pin (e.g., a strain gage) for sensing loads (e.g., forces, stresses and strains) acting on the pin. The sensor that may be attached to the inner walls of the pin may sense loads acting on the outer walls of the pine and transduce the sensed loads into electric signals. One or more LPs may be inserted (and secured) into two or more adhered structural elements, substantially perpendicular to the adhered surfaces such that no shear load is initially sensed by the LP. When the adhesion strength between the two of more structural elements is good, very little to no load may be detected by the Load Pin. When a weakening or a failure in the adhesion strength between the two or more structural elements occurs, a load (e.g., shear stress) may be applied on the Load Pin and sensed by the sensor. The alert may initiate a set of actions to deal with the coming failure, for example, reducing the speed of the vehicle, limiting the flight maneuver of an aircraft and returning the vehicle back.

Some aspects of the invention may be directed to a system for detecting weakening of the strength adhesion between two or more joint surfaces of two or more structural elements. Additionally or alternatively, the system may detect rapid separation of structural elements (e.g., a rapid detachment of the adhesion layer) due to unexpected loads applied on the structural elements. The system may include one or more Load Pins (LPs) and a controller. In some embodiments, the one or more LPs may be inserted through the two or more structural elements, perpendicular to the two or more joint surfaces such that no shear load is initially sensed by the LP. In some embodiments, the controller may be configured to upon receiving from a Load Pin (LP) a load value, detect the weakening of the adhesion strength between the two or more joint surfaces based on the load value.

Some other aspects of the invention may be directed to a method of detecting weakening of adhesion strength between two or more joint surfaces of two or more structural elements. The method may include upon receiving from a Load Pin (LP) a load value, the LP may be inserted through the two or more structural elements, perpendicular to the two or more joint surfaces such that no shear load is initially sensed by the LP; detecting the weakening of the adhesion strength between the two or more joint surfaces based on the load value.

BRIEF DESCRIPTION OF THE DRAWINGS

The subject matter regarded as the invention is particularly pointed out and distinctly claimed in the concluding portion of the specification. The invention, however, both as to system and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Some embodiments of the invention are directed to a method and a system for detecting weakening of the adhesion strength between two or more joint surfaces of two or more structural elements. Such a system may be assembled in vehicles, manned or unmanned (e.g., aircrafts, maritime vessels, UAVs and cars) in order to detect potential weakening in the adhesion strength before failure occurs. Structural elements according to embodiments of the invention may include any element, beam, support, board, sheet, cover, base, wall, part, fitting, section, piece, component or the like that may be included or assembled in a vehicle.

A system according to embodiments of the invention may include one or more Load Pins (LPs) inserted through two or more structural elements (perpendicular to the adhesion layer) and a controller (e.g., the vehicle controller). LPs according to embodiments of the invention are measurement devices having a sensor inserted inside a pin and configured to measure the load acting on the pin, as disclosed in details below. The controller may be configured to receive a load value from the LPs and determine if a weakening in the adhesion strength in the adhesion layer has occurred. The controller (e.g., vehicle controller) may further communicate with a remote station controller or processor that is associated with the vehicle (e.g., ground control station) and send an alert that a weakening in the adhesion strength has been detected.

A system according to embodiments of the invention may have compacted dimensions that may allow inserting the system anywhere in the vehicle, at any required location, regardless of the accessibility of the location.

Figure 1A:
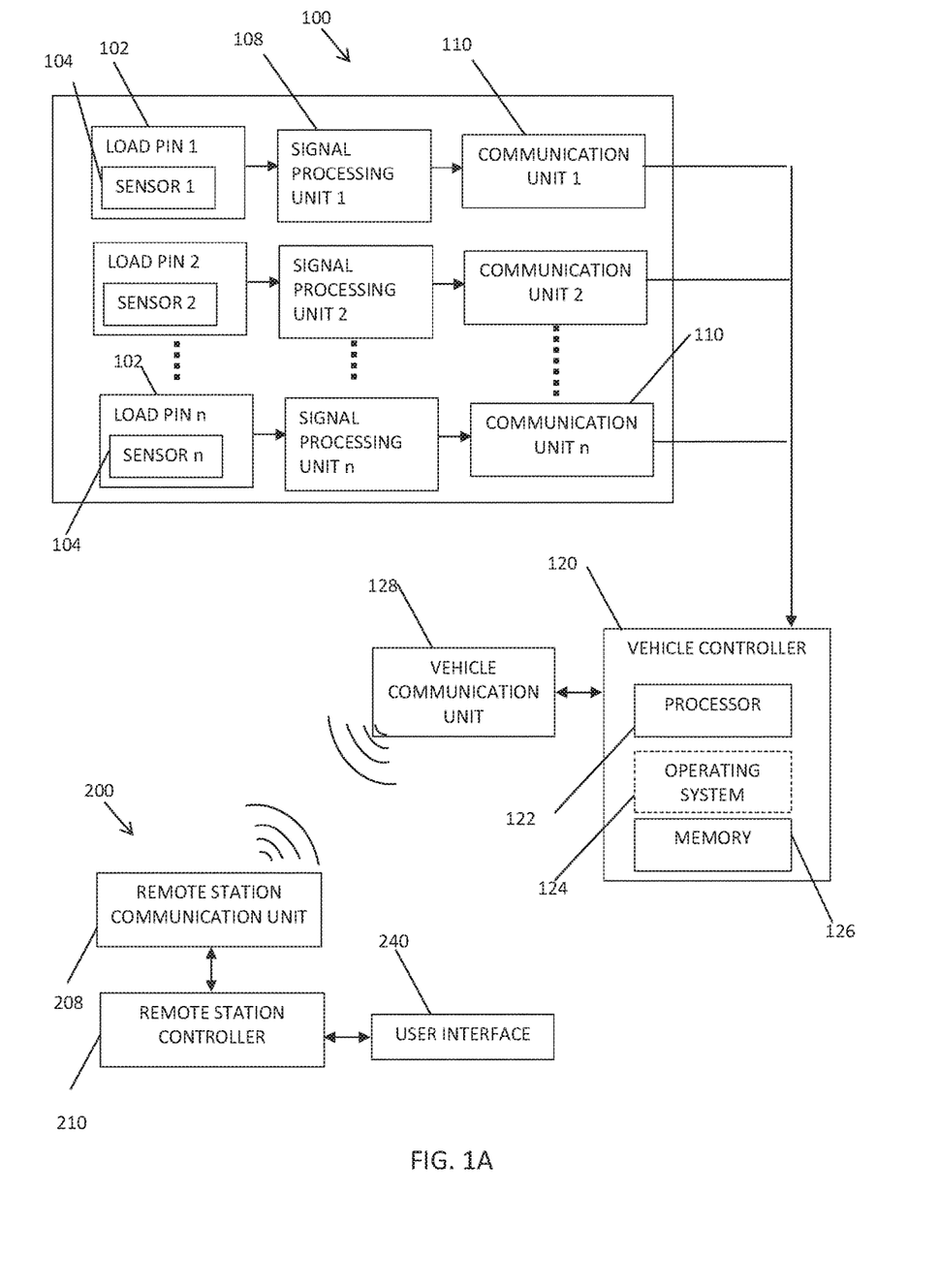
FIG. 1A is a high level block diagram of a system for detecting weakening of the adhesion strength between two or more joint surfaces of two or more structural elements included in an unmanned vehicle according to some embodiments of the invention.

Reference is made to FIG. 1A which is a high level block diagram of a system for detecting weakening of the adhesion strength between two or more joint surfaces of two or more structural elements according to some embodiments of the invention. A system 100 may be assembled in an unmanned vehicle, for example, unmanned submarines, UAVs and automatically driven cars. System 100 may include one or more Load pins (LPs) 102 and a controller 120, for example, the vehicle controller or an additional controller. In some embodiments, the LPs may be connected directly to the controller 120. In some embodiments system 100 may further include one or more signal processing unit 108 and one or more communication units 110. In some embodiments, each of signal processing unit 108 and communication unit 110 may be associated with a corresponding LP 102.

Figure 2A:
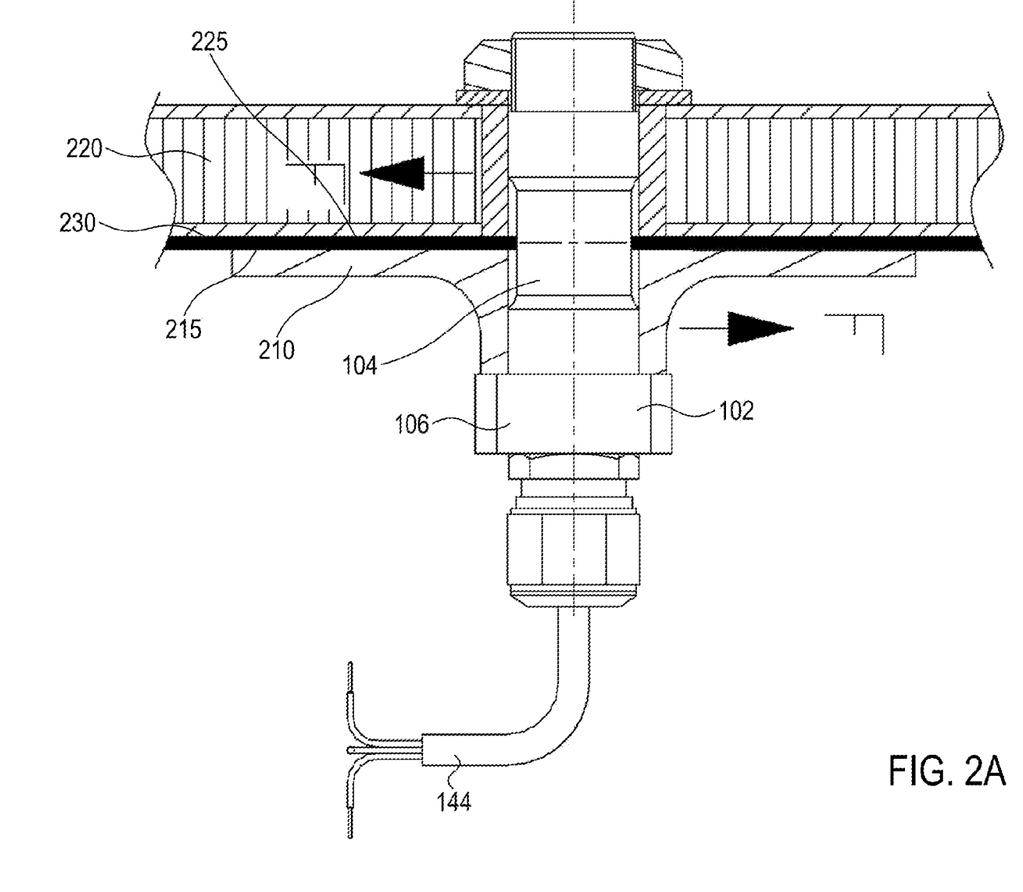
FIG. 2A is an illustration of a Load Pin (LP) inserted through structural elements according to some embodiments of the invention.
Figure 2B:
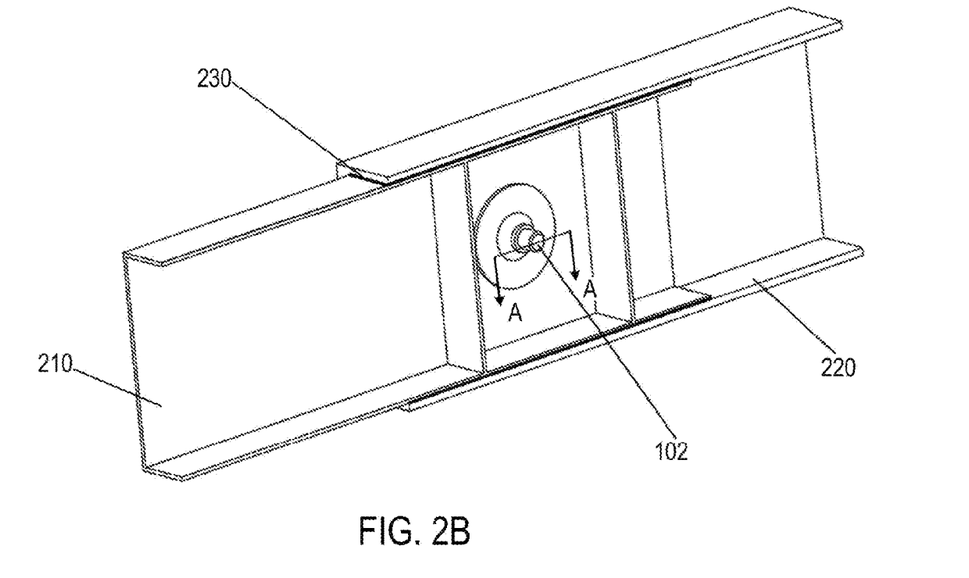
FIGS. 2B-2C are illustration of an LP located in an assembly having two or more joint surfaces of two or more structural elements according to some embodiments of the invention.
Figure 2C:
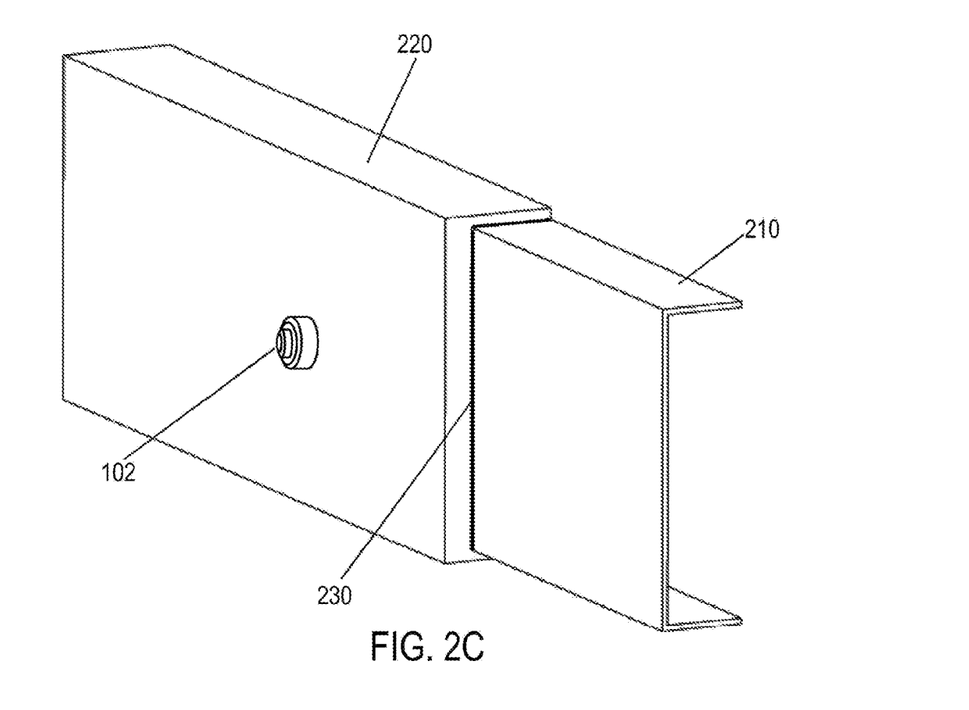

In some embodiments, LP 102 may include a sensor 104 and a pin housing 106, illustrated in FIG. 2. LP 102 may indirectly measure weakening of the adhesion strength between two or more joint surfaces. Sensor 104 may be any sensor that is configured to sense changes in load acting on the sensor, load acting on the pin or load acting in the adhesion layer. For example, sensor 104 may include a strain gauge, an optical fiber, an acoustic sensor or the like. Detailed disclosure of LP 102 when inserted through the two or more structural elements is given below with respect to FIG. 2A.

Signal processing unit 108 may be configured to process a signal received from sensor 104 such that the signal can be received and read by controller 120. For example, sensor 104 may be configured to produce an analog signal and signal processing unit 108 may transform the analog signal to a digital signal. Additionally or alternatively, signal processing unit 108 may process the signal to fit a standard communication profile, for example, to be delivered by USB. In some embodiments, signal processing unit 108 may amplify the signal received from sensor 104. In some embodiments signal processing unit 108 and the communication unit 110 may process signals coming from plurality of LPs and transfer the processed signals to the controller 120. Each signal may include the identity of each LP 102, the status of the LP (e.g., Valid/Invalid) and the load value sensed by the LP 102.

In some embodiments, signal processing unit 108 may be included in LP 102 and may be located in close proximity to sensor 104, in other embodiments signal processing 108 may be included in the controller 120 as an input/output board, and yet in some other embodiments pairs of signal processing 108 and communication units 110 might be located in midway between the LPs and the controller 120 to concentrate areas of the vehicle where several LPs are installed and communicate the LPs data to the controller 120. A signal processed by signal processing unit 108 may be transfer to controller 120 via communication unit 110. Communication unit 110 may include any device that may allow internal communication from LP 102 and/or signal processing unit 108 to the controller 120 and vice versa. For example, communication unit 110 may include communication wires connecting LP 102 and/or signal processing unit 108 to controller 120, as point to point communication or through communication bus. Alternatively, communication unit 110 may include transceivers for wireless communication between LP 102 and/or signal processing unit 108 and controller 120.

Controller 120 may be the unmanned vehicle's controller or may be an additional controller communicating with the unmanned vehicle's controller. Controller 120, may include a processor 122 that may be, for example, a central processing unit (CPU), a chip or any suitable computing or computational device, and a memory 126. Optionally, controller 120 may include an operating system 124. Controller 120 may be included or may be the vehicle's main controller. a Processor 122 may be configured to carry out methods according to embodiments of the present invention by for example executing instructions stored in a memory such as memory 126.

Operating system 124 may be or may include any code segment designed and/or configured to perform tasks involving coordination, scheduling, arbitration, supervising, controlling or otherwise managing operation of controller 120, for example, scheduling execution of programs Operating system 124 may be a commercial operating system. Memory 126 may be or may include a volatile memory and a non-volatile memory. Memory 126 may be or may include a plurality of, possibly different memory units.

Memory 126 may store any executable code, e.g., an application, a program, a process, task or script. The executable code may include data and software code for detecting weakening of the adhesion strength between two or more joint surfaces or any other code or instructions for executing methods according to embodiments of the present invention. The executable code may be executed by processor 122 possibly under control of operating system 124.

In some embodiments, controller 120 (e.g., the vehicle controller or an additional controller) may be in communication with vehicle communication unit 128. Vehicle communication unit 128 may be or may include any device (e.g., antenna, transceivers, etc.) that may allow external communication between vehicle controller 120 and a remote station 200, for example, a ground control station.

Controller 120 may be configured to automatically control the vehicle based on the signal received from LP 102. For example, if a load signal is received from LP 102 indicating weakening of the adhesion strength between two or more joint surfaces of two or more structural elements, controller 120 may automatically conduct several operations. For example, if the load signal is above a critical threshold value, controller 120 may decide to guide the vehicle to an emergency stop (e.g., an emergency landing). In yet another example, if the detected load value is above a base (e.g., normal, unloaded, etc.) value but below the critical threshold value, controller 120 may decide to monitor the load value over a predetermined length of time and as long as no increase in the load value has been detected continue with the vehicle's mission or with the vehicle current operation. If an increase in the load value has been detected, the controller may guide the vehicle to an emergency stop, guide the vehicle back to a base station, change the riding (e.g., flying, diving, etc.) parameters or the like.

Remote station 200 may include a remote station communication unit 208 for wirelessly communicating with vehicle communication unit 128, a remote station controller 210 and a remote station user interface 240. Remote station controller 210 may be any controller or processor configured to execute instructions and methods according to some embodiments of the invention. User interface 240 may be or may include any device that may allow a user to communicate with controller 210. User interface 240 may include a screen (e.g., a monitor, a display, a CRT, etc.), a pointing device and an audio device. User interface 240 may include or be associated with other input devices such as, a keyboard, a touch screen and the like. In some embodiments, controller 210 may be configured to receive from a user via user device 240 an instruction to instruct the vehicle and/or to overrule a decision made by vehicle controller 120. For example, if vehicle controller 120 made a decision to guide the vehicle to an emergency stop (e.g., an emergency landing) following a signal received from LP 102 indicating a weakening of the adhesion strength between two or more joint surfaces, a user in the remote station may decide to overrule the decision and force the unmanned vehicle to continue its mission.

Figure 1B:
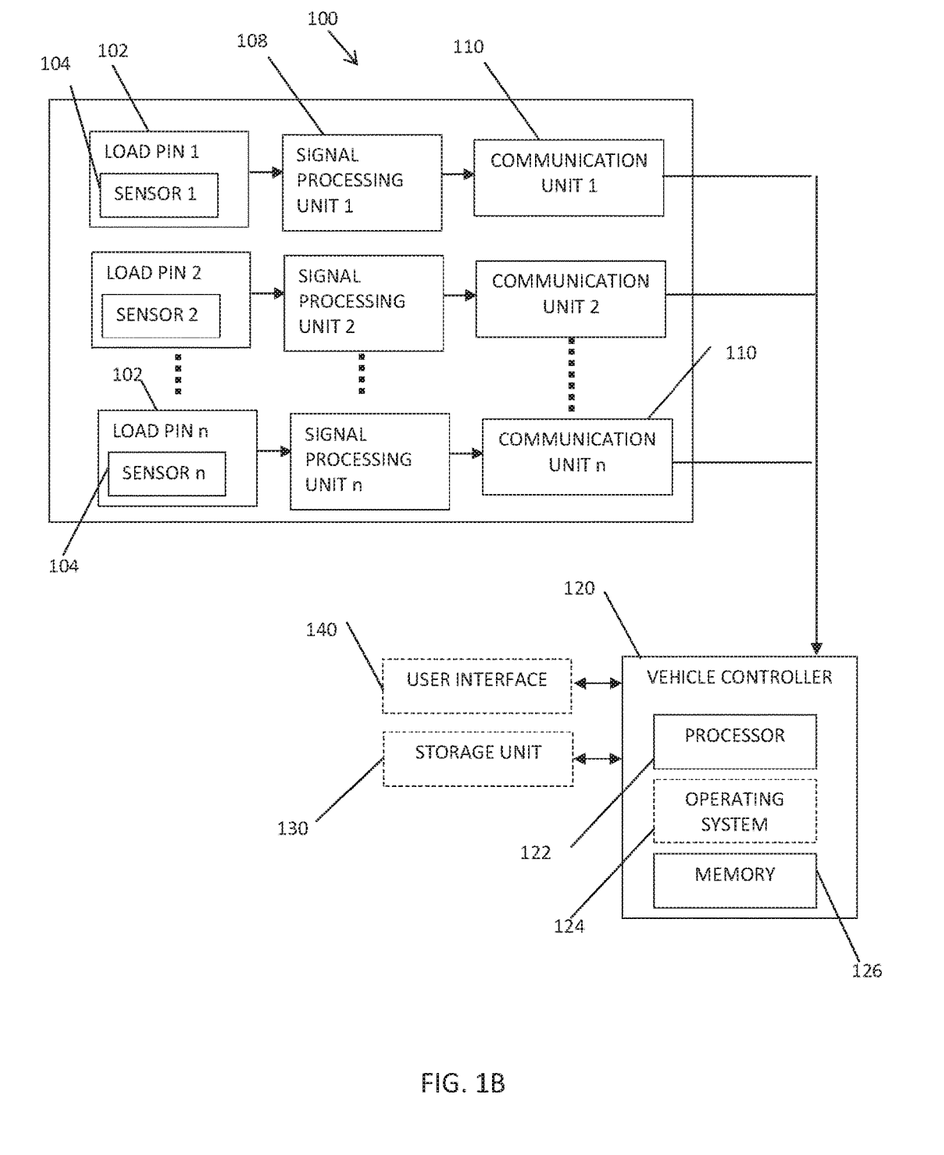
FIG. 1B is a high level block diagram of a system for detecting weakening of the adhesion strength between two or more joint surfaces of two or more structural elements included in a man-operated vehicle according to some embodiments of the invention.

Reference is made to FIG. 1B which is a high level block diagram of a system for detecting weakening of the adhesion strength between two or more joint surfaces of two or more structural elements according to some embodiments of the invention. A system 100 may be assembled in a man operated vehicle (e.g., a car driven by a driver, an aero-plan flown by a pilot, etc.). System 100 of FIG. 1B may include substantially the same elements as system 100 of FIG. 1A. System 100 may include one or more Load Pins (LPs) 102 and a controller 120, for example, the vehicle controller or an additional controller. In some embodiments, system 100 may further include one or more signal processing unit 108 and one or more communication units 110. In some embodiments, each of signal processing units 108 and communication units 110 may be associated with a corresponding LP 102. In the embodiment of FIG. 1B vehicle controller 120 may be in communication with a user interface 140 and a storage unit 130. User interface 140 may include any device that may allow a user to control the vehicle while in the vehicle. User interface 140 may include a screen (e.g., a screen on a pilot's helmet), buttons, keyboards, touchscreen, handles, a wheel, or the like. In some embodiments, controller 120 may present to the user (e.g., on a screen) an alert that a weakening of the adhesion strength between two or more joint surfaces of two or more structural elements has been detected. In some embodiments, the user may make the decision whether to continue with the mission change parameters of the mission or stop the mission or in the case of a passenger vehicle stop the drive, reduce the velocity or the like. In some embodiments, the user may ask or allow controller 120 to take the decision.

Storage 130 may store or may include data regarding past missions or data regarding the current mission that may allow controller 120 take the decision regarding the vehicle's mission. Storage 130 may be or may include, for example, a hard disk drive, a Compact Disk (CD) drive, a CD-Recordable (CD-R) drive, a universal serial bus (USB) device or other suitable removable and/or fixed storage unit. Content may be stored in storage 130 and may be loaded from storage 130 into memory 126 where it may be processed by processor 122.

In some embodiments, the system of FIG. 1B may further include a vehicle communication unit, such as unit 128 of FIG. 1A, for allowing the vehicle to communicate with a remote station (e.g., remote station 200 for command and control) in a similar way to system 100 of FIG. 1A.

Reference is made to FIG. 2 which is an illustration of a load pin (LP) inserted (and secured) through structural elements (illustrated as a cut in the structural elements) according to some embodiments of the invention. LP 102 may include sensor 104 inserted in a pin like housing 106. In some embodiments one or more LPs 102 may be inserted (and secured) through two or more structural elements 210 and 220, perpendicular to two or more corresponding joint surfaces 215 and 225. An adhesion layer 230 may be located between joint surfaces 215 and 225. Structural elements 210 and 220 may be made or may include similar or different types of materials. For example, both structural elements 210 and 220 may include composite materials. Alternatively, structure 210 may be a fitting made from metallic alloy (e.g., an aluminum alloy) and structure 210 may be a beam made from a composite material.

The single LP 102 and the two structural elements 210 and 220 illustrated in FIG. 2 are given as a simplified example only, and as it would be appreciated by one skilled in the art, that the invention is not limited to the example given in FIG. 2 (see for example, the n LP 102 illustrated in FIGS. 1A-1B). Embodiments of the invention may include any number of LPs 102 inserted in adhered assemblies comprising 2, 3, 4 or more structural elements adhered to each other.

In some embodiments, joint surfaces 215 and 225 may include different types of materials. In some embodiments, the types of material may include at least two of: composite material, metal alloys, ceramics, and plastics. In some embodiments, surface 215 may include substantially the same material as structure 210 and surface 225 may include substantially the same material as structure 220.

In some embodiments, adhesion layer 230 is constantly loaded when structural elements 210 and 220 are adhered to each other. When a weakening in the adhesion strength in layer 230 occurs, a separation or a partial separation between surfaces 215 and 225 may happen. In some embodiments, as long as the adhesion strength between surfaces 215 and 225 is above a desired level (e.g., the adhesion is good and suffices to hold structural elements 210 and 220 together) no load or substantially no load (or small load, below a predefined threshold) is applied on LP 102 and detected by sensor 104. When weakening in the adhesion strength occurs (e.g., partial separation of two or more joints surfaces 215 and 225 or complete separation of the two or more joints surfaces 215 and 225) a relative movement may be form between structural elements 210 and 220 causing for example shear stresses on pin 106 or any other load above the predefined threshold. This stress may cause sensor 104 to detect a load F (e.g., a strain, stress, force or the like) acting on LP 102. Sensor 104 may send a load value to controller 120 (illustrated in FIG. 1) via wires 144 of communication unit 110 (illustrated in FIG. 2A).

In some embodiments, one or more LPs 102 may be located at locations where failure of two or more of the joint surfaces should be identified. For example, if a computer simulation yields that at several locations in a structure high stresses may developed in the adhesion layer that may cause the layer to weaken. Accordingly, LPs 102 may be inserted to the assembly in these locations.

In some embodiments, additional attachment means may attach structure 210 to structure 220, for example, pins and/or screws and system 100 may be configured to detect a weakening in the attachment forces between structure 210 and structure 220.

In some embodiments system 100 may be assembled in a vehicle such that one or more LPs (e.g., LPs 102) are inserted through at least two structural elements adhere to each other included in the vehicle. Additionally, controller 110 may be configured to communicate with a processor associated with the vehicle to alert the processor of the detected weakening of the adhesion strength between the at least two structural elements.

Figure 3:
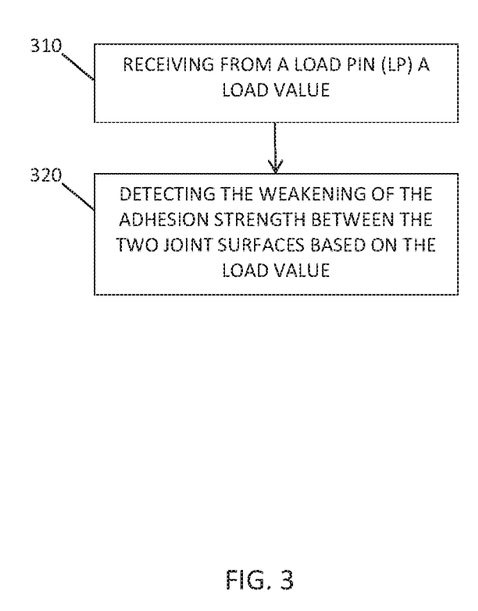
FIG. 3 is a flowchart of a method of detecting weakening of the adhesion strength between two or more joint surfaces of two or more structural elements according to some embodiments of the invention.

Reference is made to FIG. 3 which is a flowchart of a method of detecting weakening of the adhesion strength between two or more joint surfaces of two or more structural elements according to some embodiments of the invention. Embodiments of the method of FIG. 3 may be performed by a controller such as controller 120 (e.g., by processor 122 included in a vehicle's controller) or by any other suitable controller or processor. In operation 310, embodiments may include receiving from an LP (e.g., LP 102) a load value. In some embodiments, the LP may be inserted through the two or more structural elements (e.g., structural elements 210 and 220), perpendicular to the two or more joint surfaces (e.g., surfaces 215 and 225). The load value may include a reading received from a sensor (e.g., sensor 104) included in LP (e.g., LP 102). The load value may include a strain value, a force value, a stress value, or the like. The load value may indicate that a force F (e.g., the sheer force) was applied on pin-like housing (e.g., LP housing 106 of LP 102).

In some embodiments, the two or more joint surfaces may be subjected to dynamic loads during the service life of the two or more structural elements. For example, structural elements 210 and 220 may be included in a vehicle and adhesion layer 230 between joint surfaces 215 and 225 may be subject to dynamic loads when the vehicle is on the move (e.g., fly, drive, etc.). In some embodiments, the vehicle may be subjected to an extreme loads (e.g., air turbulence, G forces etc.) when the vehicle is on the move. These dynamic and/or extreme loads may affect the adhesion strength over time and may cause weakening of the adhesion strength or even a complete failure, in addition to other effects for example, due to fatigue, aging of the materials included in adhesion layer 130, non-uniformity in adhesion layer 130 (during production) and the like.

In operation 320, embodiments may include detecting the weakening of the adhesion strength between the two or more joint surfaces based on the load value. In some embodiments, weakening of the adhesion strength in the two or more joint surfaces includes at least one of: partial separation of the two or more joints surfaces and complete separation of the two or more joints surfaces. In some embodiments, the complete separation may be a rapid separation that may cause a complete failure of the structural elements. In some embodiments, the indication of the weakening of the adhesion strength in the two or more joint surfaces is received when the LP indicates increasing of the load value. For example, as long as there is a good adhesion between surface 215 and surface 225 (e.g., adhesion layer 230 is loaded and substantially without defects) no load or an initial lower load value may be sensed by LP 102. When a separation or partial separation occurs there may be an increase in the force F applied on LP 102, thus an increase in the load value may be detected by LP 102. Measuring the increase in the load value sensed by sensor 104 of LP 102 is an indirect measurement of the weakening of the adhesion strength in the two or more joint surfaces. This indirect measurement may be further indicative of a change in the adhesion strength of the adhesion layer 230. When adhesion layer is affected by a partial separation or a complete separation there is a change in the load inside adhesion layer 230. As oppose to known prior art methods that directly sense the changes in the load in adhesion layer 230 by placing sensors in the adhesion layer, embodiments of the current invention are using an indirect measurement of the change in the load in adhesion layer 230 or the weakening of the adhesion strength in adhesion layer 230.

In some embodiments, the method may further include making an operational decision based on the detected load value. In some embodiments, when the detected load value is above a predetermined critical threshold value that may indicate high probability of failure, controller 120 may be configured to guide or direct the vehicle to make an emergency stop. For example, controller 120 may guide an UAV for an emergency landing, cause an unmanned submarine to rise to the sea level or call a race car to return to the pit station. In some embodiments, the detected load value may be between the base value and the critical threshold value, meaning that a weakening in the adhesion strength has occurred, but the probability of failure is not high. In such a case, controller 120 may be configured to monitor the load value over a predetermined amount of time to detect an increase in the load value. As long as no increase has been detected, controller 120 may decide to continue with the vehicle's mission. Controller 120 may further send a remote station (e.g., remote station 200) an alert to check the quality of the adhesion between the structural elements when the vehicle returns from its' mission (e.g., checking a UAV or submarine on the ground in a workshop). If an increase in the load value has been detected, controller 120 may decide to change parameters of the mission (e.g., reduce the flying height, avoid sharp maneuvering, reduce diving depth, reduce velocity, shortening the mission for early return to maintenance, etc.) or may guide the vehicle to an emergency stop.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of detecting weakening of adhesion strength between two or more joint surfaces of two or more structural elements, comprising:
    receiving from a Load Pin (LP) a shear load value, wherein the LP is inserted through the two or more structural elements, perpendicular to the two or more joint surfaces, and wherein a shear load initially sensed by the LP is substantially zero; and
    detecting the weakening of the adhesion strength between the two or more joint surfaces when the received shear load value is substantially non-zero.

2. The method according to claim 1, wherein weakening of the adhesion strength in the two or more joint surfaces includes at least one of: partial separation of the two or more joints surfaces and complete separation of the two or more joints surfaces.

3. The method according to claim 1, wherein the indication of the weakening of the adhesion strength in the two or more joint surfaces is received when the LP indicates increasing of the shear load value.

4. The method according to claim 1, wherein the two or more joint surfaces include metal alloys.

5. The method according to claim 1, wherein the two or more joint surfaces include different types of materials.

6. The method of claim 5, wherein the types of material includes at least two of: composite material, metal alloys, ceramics, and plastics.

7. The method according to claim 1, wherein the LP includes at least one of: an optical fiber, strain gauge and acoustic sensor.

8. The method according to claim 1, wherein the two or more joint surfaces are subjected to dynamic loads.

9. A system for detecting weakening of adhesion strength between two or more joint surfaces of two or more structural elements, comprising:
    one or more Load Pins (LPs), wherein the one or more LPs are inserted through the two or more structural elements, perpendicular to the two or more joint surfaces and wherein a shear load initially sensed by the LPs is substantially zero; and
    a controller configured to:
        upon receiving from the one or more LPs a substantially non-zero shear load value,
        detect the weakening of the adhesion strength between the two or more joint surfaces.

10. The system according to claim 9, further comprising a communication unit for sending signals received from the LPs to the controller.

11. The system of claim 10, wherein the communication unit is at least one of: wired communication and wireless communication.

12. The system according to claim 9, wherein the one or more LPs are inserted through at least two structural elements adhered to each other, wherein said at least two structural elements form a part of a vehicle.

\* \* \* \* \*